Figure 1:
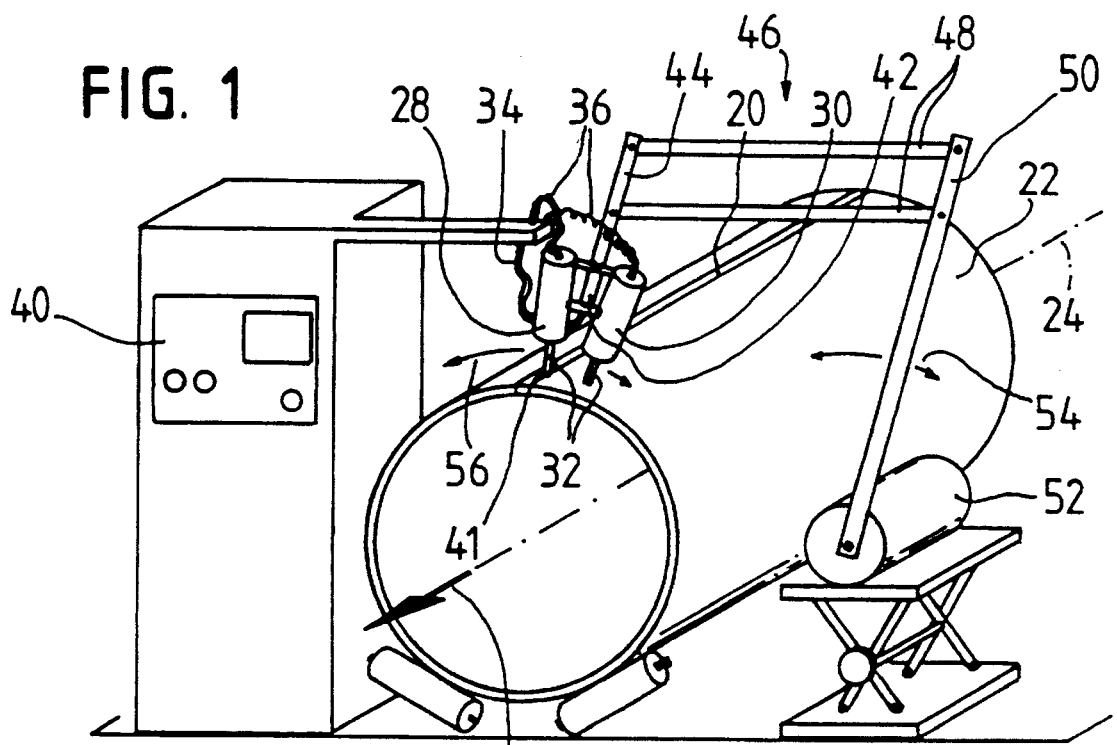

United States Patent [19]

Karbach et al.

[11] Patent Number: 5,583,292
[45] Date of Patent: Dec. 10, 1996

[54] ULTRASONIC MEASURING PROCESS FOR THE WALL THICKNESS CURVE OF A WELD SEAM OF A PIPE

[75] Inventors: Bernhard Karbach, Erttstadt-Friesenheim; Siegmar Schulz, Köln; Peter Steinert, Kerpen, all of Germany

[73] Assignee: Krautkramer GmbH & Co., Germany

[21] Appl. No.: 119,152

[22] PCT Filed: Jul. 16, 1991

[86] PCT No.: PCT/DE91/00578

§ 371 Date: Sep. 23, 1993

§ 102(e) Date: Sep. 23, 1993

[87] PCT Pub. No.: WO92/16832

PCT Pub. Date: Oct. 1, 1992

[30] Foreign Application Priority Data

Mar. 23, 1991 [DE] Germany .................. 41 09 625.8

[51] Int. Cl.⁶ .................................................. G01N 29/04
[52] U.S. Cl. ..................................... 73/638; 73/588
[58] Field of Search .......................... 73/588, 598, 638, 73/640, 641, 622, 628, 643, 644

[56] References Cited

U.S. PATENT DOCUMENTS

| | | | |
|---|---|---|---|
| 2,953,017 | 9/1960 | Bincer et al. | 73/640 |
| 3,255,626 | 6/1966 | Van Der Veer | 73/71.5 |
| 3,350,925 | 11/1967 | Coy | 73/638 |
| 3,485,088 | 12/1969 | O'Conner | 73/67.8 |
| 3,908,455 | 9/1975 | Olson et al. | 73/167 |
| 4,131,027 | 12/1978 | Terschüren et al. | 73/638 |
| 4,312,230 | 1/1982 | Bricker et al. | 73/638 |
| 4,351,190 | 9/1982 | Rehme et al. | 73/638 |
| 4,403,510 | 9/1983 | deWalle et al. | 73/644 |
| 4,467,654 | 8/1984 | Murakami et al. | 73/640 |
| 4,475,399 | 10/1984 | Livingston | 73/638 |
| 4,531,409 | 7/1985 | Koch et al. | 73/588 |
| 4,586,379 | 5/1986 | Burkhardt, Jr. | 73/638 |
| 4,627,289 | 12/1986 | Fukuda et al. | 73/638 |
| 4,665,734 | 5/1987 | Joet | 73/638 |
| 4,672,852 | 6/1987 | Gugel et al. | 73/638 |
| 4,700,572 | 10/1987 | Senba et al. | 73/638 |
| 5,007,291 | 4/1991 | Walters et al. | 73/638 |
| 5,329,561 | 7/1994 | Desruelles | 73/588 |

FOREIGN PATENT DOCUMENTS

| | | |
|---|---|---|
| 0334053 | 9/1969 | European Pat. Off. . |
| 119096 | 9/1984 | European Pat. Off. . |
| 159830 | 6/1970 | France . |
| 8000616 | 4/1980 | WIPO . |

*Primary Examiner*—Richard Chilcot
*Assistant Examiner*—Eric S. McCall
*Attorney, Agent, or Firm*—Eckert Seamans Cherin & Mellott

[57] ABSTRACT

An ultrasonic measuring process is disclosed for measuring the wall thickness variation in the region of the welding seam of a pipe. At least two testing heads are each acoustically coupled to the pipe by a water jet. The acoustic entry zones of the testing heads are moved together in relation to the pipe, parallel to the axis of the pipe. At least one of the testing heads is moved back and forth across the axis of the tube, crossing over the welding seam. The acoustic entry zone can be moved by modulation of a phased array. The second testing head either emits acoustic radiation into the pipe always outside the welding seam or also crosses the welding seam, but at different times than the first testing head. The signals of both testing heads are processed in a measurement value processing circuit such that simultaneously occurring measurement value deviations supply no output signal.

15 Claims, 3 Drawing Sheets

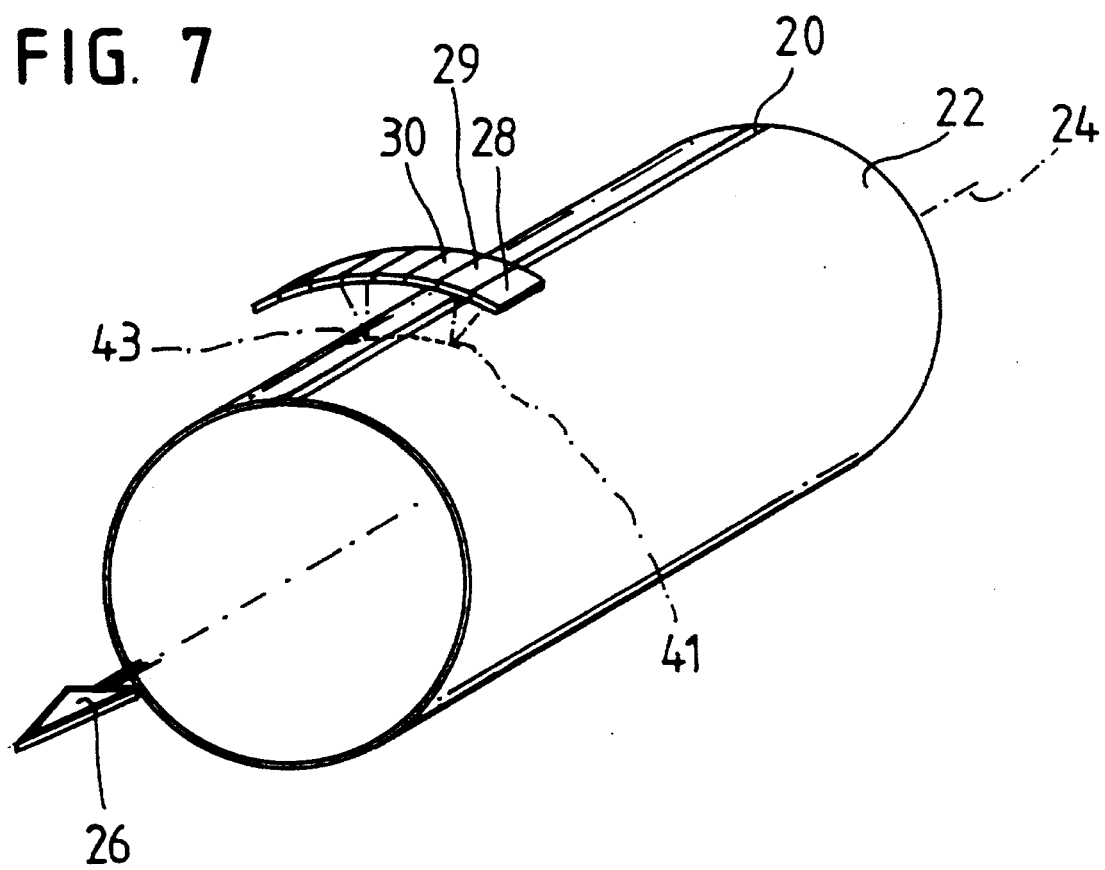

ULTRASONIC MEASURING PROCESS FOR THE WALL THICKNESS CURVE OF A WELD SEAM OF A PIPE

The invention pertains to an ultrasonic measuring process for the wall thickness curve of a weld seam of a pipe, especially a pipe with a shaved weld seam, wherein an ultrasonic oscillator is coupled acoustically to the pipe via a hydraulic buffer, from it ultrasonic impulses enter in an acoustic entry zone into the pipe, the reflected components of these pulses from the ultrasonic oscillator are received again and fed as an electrical signal to a measured value processing circuit, the ultrasonic oscillator is moved relative to the pipe parallel to the pipe axis and the acoustic entry zone is moved back and forth transversely to the pipe axis in such a way that the weld seam and the peripheral regions to the left and right of the weld seam are passed over; the invention also pertains to devices for execution of this measurement process.

In a welded pipe, the wall thickness curve in the region of the weld seam generally deviates from the curve of the wall thickness of the remaining cross section of the pipe. The goal in the production of a welded pipe is that the wall thickness curve differ as little as possible, preferably not at all, from the wall thickness curve outside of the weld seam so that the welded pipe differs as little as possible from an ideal cylindrical pipe.

Without reworking, the weld seam is generally thicker than the wall thickness of the coil from which the pipe is manufactured. In this process it is attempted to have the weld seam protruding both to the outside and to the inside relative to ideal cylinder geometry, i.e. to be convex. The weld seam can be taken down by reworking, especially shaving, to such an extent that the ideal cylindrical curve is present on the outside and the inside.

During welding, defects may appear; despite the greater wall thickness in the region of the weld seam, the outside contour may run concavely, the inner contour will then have a relatively strong convex curvature. Furthermore, small irregularities in the longitudinal direction of the weld seam, e.g., waves or ribs, may appear.

As a result of the secondary treatment which is summarized in the following under the concept of shaving, material is removed on the outside and inside with the purpose of configuring the cross-sectional curve in such a way that an ideal purely cylindrical pipe geometry is present. The shaving is generally performed with a chisel: an external chisel is used for outside shaving and an internal chisel is used for inside shaving. Both are arranged at a certain distance behind the welding device of a conventional type and need not be discussed further here. If deviations appear during the shaving, e.g., if the attitude of the chisel changes, the chisel wears down or breaks, the pipe geometry will deviate from the sought ideal curve. Typical in such case are shaving operations which are conducted a little above the actual ideal pipe contour and result in sharp edged "steps" in the cross-sectional curve of the pipe. Another deviation involves shaving off too much, causing the pipe then to be flattened out in the cross-sectional curve at the weld seam.

A weld seam test of the type mentioned initially is known which operates by means of a hydraulic-coupled ultrasonic oscillator. This ultrasonic measurement process, however, does not operate with the accuracy required for testing of reworked weld seams. Thus it is difficult to register the geometries of shaved pipes in which the wall thickness in the curve of the weld seam although just as large as that beside the weld seam, nevertheless deviates from the ideal curve of cylindrical geometry, because the outside shaving, for example, has caused flattening and a certain convexity was preserved during the inside shaving. But in particular, according to the previously known ultrasonic measurement procedures, steps, especially small steps in the cross-sectional curve of the pipe cannot be demonstrated with certainty. The transportation of the pipe by the conveyer mechanism always takes place with a certain irregularity. The pipe being conveyed usually executes small movements transversely to its longitudinal axis which may be periodical or nonperiodical. Periodical movements occur, for example, as a result of worn guide rolls. According to the previously known process, it is impossible to distinguish between guidance inaccuracies and geometric deviations of the same magnitude, e.g., small steps in the cross-sectional curve of the welded pipe.

The requirements imposed on the geometry of welded pipes are specified by the receiver and by the intended application purpose. If welded pipes are to be used, e.g., for exhaust systems, deviations from the ideal geometry may lead to flow variations in the exhaust gases which impair the efficiency of the exhaust system, especially in an exhaust system with a catalyst.

In the ultrasonic measuring process of the type mentioned initially the ultrasonic oscillator is not guided directly on the pipe. When the ultrasonic oscillator is guided directly on the pipe a constant buffer distance must always be present so that deviations from the ideal cylindrical geometry, e.g., flattening due to outside shaving cannot be registered. The previously known measurement process, therefore, operates with a movement device which moves the ultrasonic oscillator without direct guidance, therefore freely, relative to the pipe. The free oscillation, however, has the disadvantage that the above described changes in position (e.g., vibrations) of the pipe also change the hydraulic buffer path and can therefore simulate geometry errors. The sound is emitted radially so that the pipe wall is impinged vertically.

Starting with the measuring process of the type mentioned initially, the invention has the task of avoiding the disadvantages of this known process and the device operating according to it and improving both the process and the apparatus in such a way that the relative movements of the pipe transversely to the ideal (theoretical) central axis of the pipe have no effect on the measured value so that even small steps in the wall thickness can be registered in the cross-sectional curve of a reworked welded pipe.

This problem is solved by starting with the ultrasonic measuring process of the type mentioned initially by arranging a second ultrasonic oscillator, which is also coupled acoustically to the pipe via a hydraulic buffer, in the vicinity of the first ultrasonic oscillator, exposing the pipe to ultrasonic pulses and sending the reflected components of said pulses as electrical signals to the measured value processing circuit, said second ultrasonic oscillator executing at least axial motion relative to the pipe together with the first ultrasonic oscillator; the two ultrasonic oscillators are never located above the weld seam at the same time, and the signals of the two ultrasonic oscillators are processed in the measured value processing circuit in such a way that measured value deviations occurring within a time span which is so brief that practically no additional mechanical change in position of the pipe can take place in it deliver no output signal.

According to the invention, therefore, a second ultrasonic oscillator is provided which is also not guided directly on the pipe and is held either independently of the first ultrasonic oscillator by its own mechanism or is rigidly connected to it, e.g., in the form of two individual test heads or in the form of an array, especially a phased array. In the first case, its own mechanism, e.g., is stationary, so that the second ultrasonic oscillator always scans the pipe on the outside of the weld seam and is therefore capable of registering positional changes of the pipe. Any change in position registered by it is subtracted from the signal of the first ultrasonic oscillator in the measured value processing circuit so that positional changes in the pipe being tested have no effect on the output signal.

In the case of an also moving second ultrasonic oscillator, the movement mechanism of the second ultrasonic oscillator is matched to the movement mechanism of the first ultrasonic oscillator in such a way that the ultrasonic oscillators pass over the weld seam at different times. The two ultrasonic oscillators are arranged, when viewed in the cross sectional plane of the pipe, in such a way that they emit sound into the pipe along the pipe circumference in an offset manner. In addition, they may also be offset with respect to one another axially (in the direction of the pipe). The offset should be selected to be as small as possible. The two ultrasonic oscillators are supposed to beam sound into the pipe at positions as close together as possible in order for the movements of a partial region of the pipe relative to another partial region not to lead to a falsification of the measurement result.

In the case of a separate but not back-and-forth-moving second ultrasonic converter, the latter is used only for compensation of the relative movements of the pipe. If the second ultrasonic oscillator also moves back and forth, it also emits a signal over the geometric curve of the weld seam which, to be sure, is offset in time relative to the signal of the first ultrasonic oscillator. The two signals can therefore be combined with one another by a suitable known procedure in such a way that a single statement is obtained concerning the curve of the weld seam at the measured position.

The arrangement of several ultrasonic oscillators into a linear array has been found to be especially favorable, in which case the individual ultrasonic oscillators are arranged tangentially to a radial plane of the pipe so that their central beams intersect the longitudinal axis of the pipe at a single point. Back and forth movement of the ultrasonic oscillator is not necessary; rather the array, preferably a phased array, is modulated electronically in such a way that the acoustic entry zone on the outer skin of the pipe is moved back and forth, passing over the weld seam. The back and forth movement and the scanning behavior are selected in such a way that—as in the previously described case of separate ultrasonic oscillators—reference values outside of the weld seam and values from the weld seam itself are present. In this case the briefest possible measuring time is selected so that between the registration of a reference value and a measurement in the region of the weld seam no significant movement of the pipe can have taken place. As opposed to the previously described design with two separate ultrasonic oscillators, which are preferably operated simultaneously, in the case of an array the emission of two pulses at the same time is impossible. To be sure, two pulses can be emitted in such brief succession and received again that no significant movement of the pipe can have occurred in the intervening time. Pipe movements take place within a time greater than 0.1 s. Measured values which are collected in a shorter time are therefore practically not influenced by a pipe movement.

Relative changes in the pipe, therefore positional changes, vibrations, etc., cannot influence the results of the measurements according to the invention. External shaving effects or other deviations from the exterior ideal cylindrical geometry are registered by a change in the hydraulic buffer, therefore the entry echo in the output signal is time shifted.

The wall thickness can be obtained by the known method from the time difference between the entry echo and the back wall echo. In this way the wall thickness curve can be represented. The wall thickness curve includes, on the one hand, deviations of the outer contour from the ideal cylindrical geometry and, on the other hand, deviations of the inner contour from the ideal cylindrical geometry, with both deviations being registered independently of one another.

The problem posed is mechanically solved by an apparatus according to the invention.

In a preferred modification, both ultrasonic oscillators are offset circumferentially with respect to each other at least by the width of the weld seam (shaving width). In this way only one ultrasonic oscillator will scan the reworked weld seam; there are never two ultrasonic oscillators simultaneously coupled to the shaved region.

Advantageously, the ultrasonic oscillators are acoustically coupled to the pipe via water jets. Ultrasonic oscillators of this type with a free water jet for contactless coupling are described, e.g., in the book by J. and H. Krautkrämer "Werkstoffprüfung mit Ultraschall", 4th edition, Springer Verlag, in U.S. Pat. Nos. 3,255,626, 3,485,088, 3,908,455 and 4,403,510 and in EP Patent 119 096. In an advantageous version, a common somewhat wider water jet can be used for both ultrasonic oscillators or at least both ultrasonic oscillators are connected via the same hydraulic conveyer so that the functional security of the installation is increased. The coupling of each individual ultrasonic oscillator can be monitored by known methods by measuring the entry echo.

In mechanical terms, it has been found to be advantageous in the design of a jointly moving second ultrasonic oscillator to arrange the two ultrasonic oscillators on the same holder which executes a motion on an arc of circle around the axis of the pipe segment by means of a common movement mechanism. Relative movements of the two ultrasonic oscillators with respect to each other are prevented. Parallelogram guides have been found to be very suitable for the movement mechanism, especially since they can be adapted relatively rapidly to different pipe dimensions.

Figure 2:
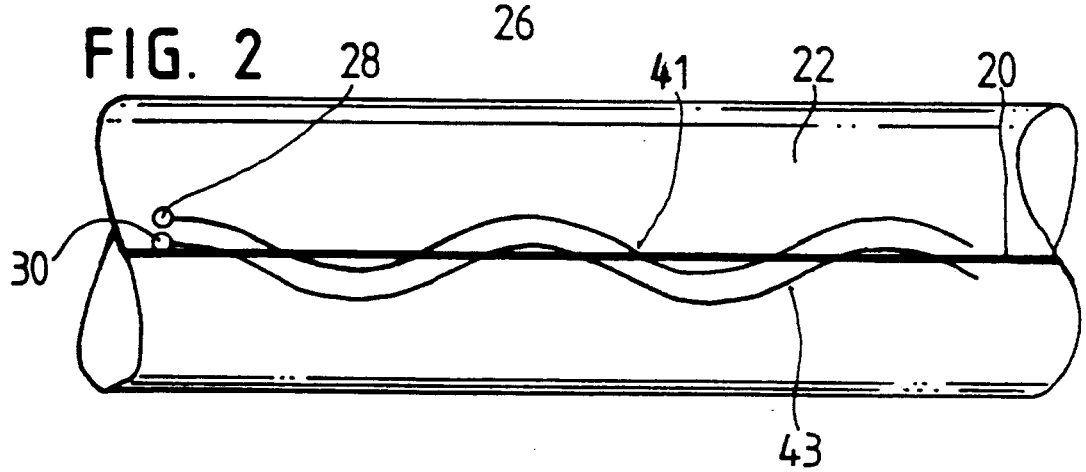
Figure 3:
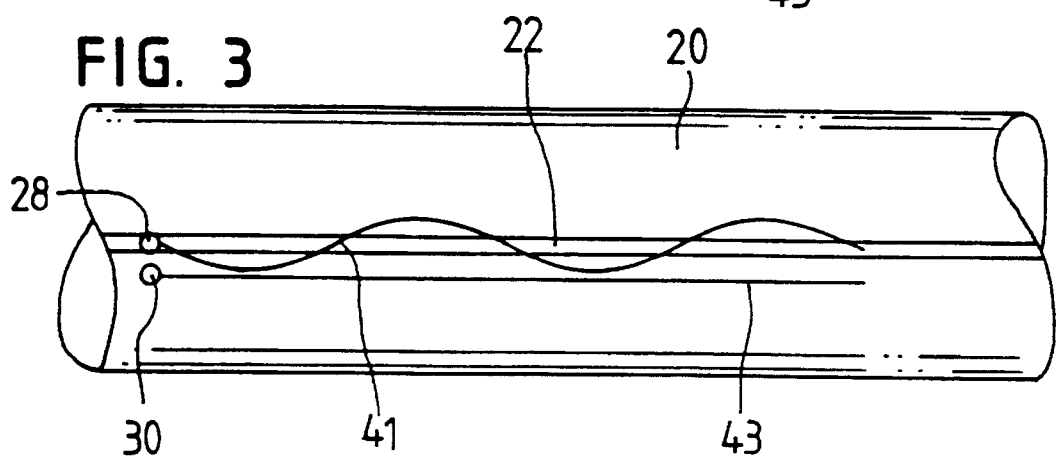
Figure 4:
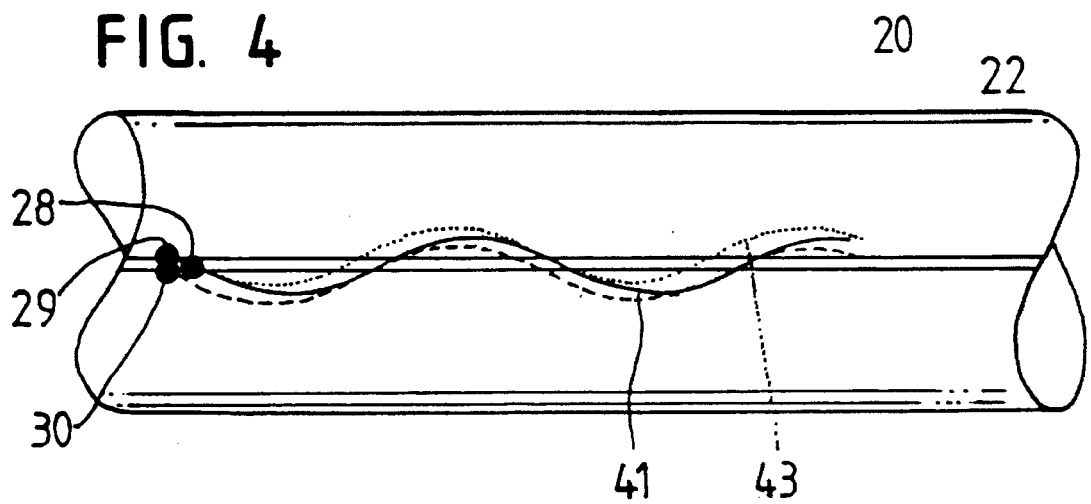

Other advantages and features of the invention may be obtained from the remaining claims and from the description below of examples of embodiment of the invention which are not limiting and which are illustrated in detail with reference to the drawing, in which:

FIG. 1 shows a perspective view of an apparatus for ultrasonic measurement of the wall thickness curve of a weld seam of pipe, FIG. 2 is a top view of a pipe as in FIG. 1 explaining the curve of the test tracks which are plotted in, FIG. 3 is a view corresponding to FIG. 2 for another version of the mechanism, FIG. 4 is a representation corresponding to FIG. 2 but for a mechanism with three ultrasonic oscillators arranged in a V pattern.

Figure 5:
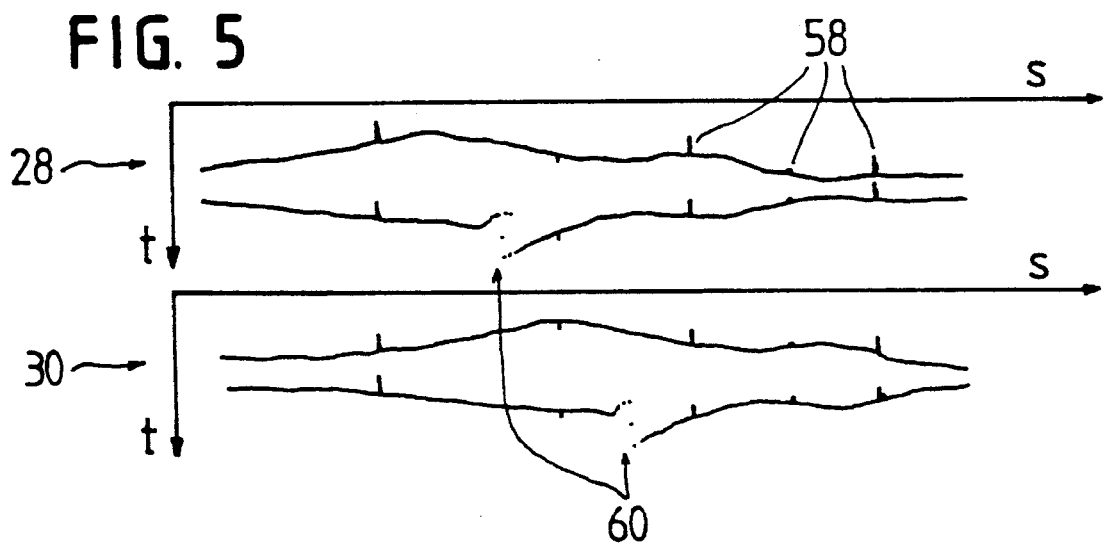
Figure 6:
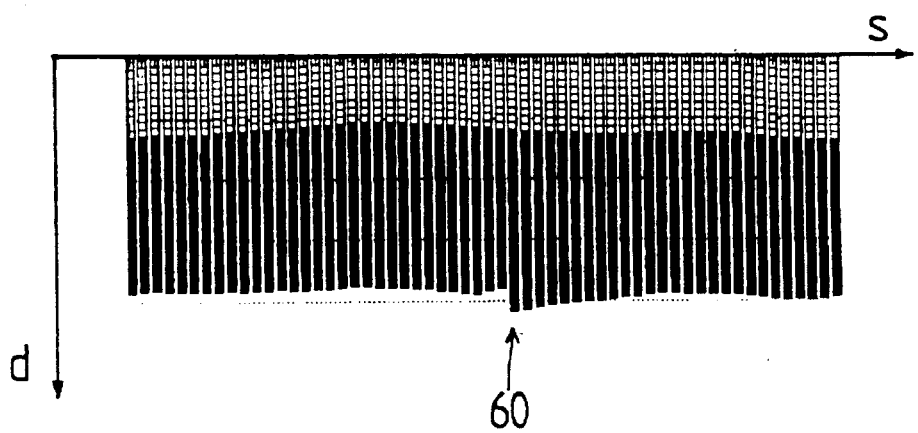

FIG. 5 is a diagram of the time curve t of the entry of the echo into the outer wall of the pipe and the inner wall of the pipe plotted against the test distance for two ultrasonic oscillators, FIG. 6 is the wall thickness curve d found from the data in FIG. 5 (solid lines) and the hydraulic buffer, again plotted against the test path s, and FIG. 7 is a perspective view as in FIG. 1 of a pipe being tested with a test head constructed from several ultrasonic oscillators in the form of an array.

In FIG. 1 a mechanism is shown schematically for the ultrasonic measurement of the wall thickness curve of a weld seam 20 of a pipe 22. The pipe 22 is produced by the conventional method from a coil or other suitable sheet metal blank in an endless process. The blank is curved into an open pipe, the narrow opposing edges are joined together along the weld seam 20, thus forming the pipe 22.

Shortly behind the welding mechanism (not shown, since it is well known) is an also not shown, since well known, mechanism for reworking. It usually has an outer and an inner chisel. The outer chisel shaves the outside and the inner chisel shaves the inside. The shaving is supposed to be performed in each case in such a way that the smallest possible deviation from ideal pipe geometry appears in the region of the weld seam when viewed in cross section.

According to the process of the invention, the wall thickness curves in the region of the weld seam 20 can be registered for production control in order to avoid rejects due to defective welding, but especially because of defective shaving.

The welded pipe 22 is situated on a conventional mechanism for guidance and axial conveying which is not shown here in detail, the conveying taking place in the direction of the directional arrow 26 which coincides with the longitudinal pipe axis 24. The weld seam 20 is situated at the highest point on the pipe 22, generally described as the 12 o'clock position. The weld seam may deviate from this position as a result of production factors.

Above the pipe 22 are two ultrasonic oscillators 28, 30 which are designed as separate testing heads and which are both aligned in such a way that they beam sound on a radial line into the walls of the pipe 22. Expressed in other terms, in operation of the ultrasonic oscillators 28, 30, in each case the central beam of the emitted ultrasonic pulse moves on a line which runs at right angles to the longitudinal pipe axis 24 and intersects it.

The two ultrasonic oscillators 28, 30 do not touch the pipe 22 mechanically, rather they are located a free distance above the pipe which amounts, e.g., to 5 to 50 millimeters. The ultrasonic oscillators 28, 30 in each case are acoustically coupled to the pipe 22 via a hydraulic buffer 32 in the form of a water jet. Ultrasonic oscillators with water jet coupling are already well known and are called "bubblers" in the technical jargon. Through a common flexible hydraulic feed line 34 the two ultrasonic oscillators 28, 30 are supplied with water, the water flows through the rigid mechanical connection 42 of the two ultrasonic oscillators 28, 30 and then flows down in the direction of the main beam of the ultrasonic oscillator. In addition, each ultrasonic oscillator is electrically connected through a flexible lead wire 36 to a control unit 38 in which for each ultrasonic oscillator 28, 30 a transmitter and a measured value processing circuit 40 are situated. The hydraulic line 34 and the feed line 36 are supported and carried by a boom.

Both ultrasonic oscillators 28, 30 can be adjusted by conventional means with respect to their rigid mechanical connecting piece 42 in the radial plane of the pipe 22 and transversely to it in order to achieve the described alignment of the central beams. On the connecting piece 42 in the center an arm 44 of a parallelogram arrangement 46 is rigidly seated. The latter additionally has two parallel running follower arms 48 of the same length hinge-jointed at one end to the arm 44 and one drive arm 50 also hinge-jointed to the follower arms 48 running parallel to the arm 44. The latter is longer than the arm 44 and terminates in a horizontal plane which runs through the longitudinal pipe axis 24 and at a distance the length of the follower arms 48 from the longitudinal pipe axis 24. There the shaft of a drive motor 52 is situated which is designed as a stepping motor. The length of the arm 44 is selected such that the ultrasonic oscillators 28, 30 at the said free distance from pipe 22 are moved back and forth on a concentric segment of a circular arc. This is done by moving the driving arm 50 back and forth in the direction of the arrow 54, the reciprocating movement of the ultrasonic oscillators 28, 30 themselves is represented by the double arrow 56. The movement is carried out in such a way that both ultrasonic oscillators 28, 30 cross the weld seam 20 and both sides of said weld seam 20 register undisturbed regions of the pipe wall not influenced by the welding. The ultrasonic oscillators 28, 30 operate in the pulse echo mode; therefore they emit brief sound pulses whose reflections (echoes) are redetected and transformed into an electrical signal to be sent to the measured value processing circuit 40.

The main beams of the two ultrasonic oscillators 28, 30 are situated in the same radial plane, although offset along the circumference of the pipe 22. The distance from the acoustic entry zones 41, 43 of the two ultrasonic oscillators 28, 30 from one another is as small as possible but greater than the width of the weld seam 20.

The practical sequence of execution of the ultrasonic measuring process for the wall thickness curve of a weld seam of a pipe is described in the following, this description serving also to explain the ultrasonic measuring process: the pipe 22 is conveyed forward (out of the plane of the picture) in the direction of the arrow 26 and thus in the direction of its longitudinal axis 24. This conveying does not always take place free of vibration, rather periodically and nonperiodically disturbances arise, the pipe 22 may possibly change its position, vibrate, experiences jolts due to worn drive rolls, etc.

Due to the swiveling back and forth of the drive arm 50 driven by motor 52 the two ultrasonic oscillators 28, 30 are moved on an arc of a circle whose midpoint lies in the longitudinal axis 24 of the pipe. During forward motion they successively pass over the weld seam 20 and also during the reverse motion. At this time the acoustic entry zones 41, 43 describe a curve such as is shown in FIG. 2. This curve is, in other words the site of the points where the central beams strike the pipe skin. The paths shown by solid lines of the ultrasonic oscillators 28, 30, called the test track in the following, consist in reality of a large number of individual test points lying side by side, since pulses are constantly being fed at a high frequency into the pipe 22.

As a result of an emitted ultrasonic pulse, the ultrasonic oscillator 28 or 30 in each case receives the so called entry echo, therefore the reflection of the emitted pulse on the skin surface of the pipe 22 as well as the so called back wall echo, i.e., the reflection on the inner wall of the pipe 22. The duration of time when an entry echo appears after the emission of the pulse depends on the length of the hydraulic buffer 32. The duration of time when the back wall echo appears depends, in addition to the length of the hydraulic buffer 32, also on the thickness of the wall of the pipe 22. From the two measurement data, therefore the geometric location of the acoustic entry point into the pipe and the geometric location of the inner wall are known so that from a series of ultrasonic measurements (shots) the geometric curve of the wall thickness can be stated.

The two ultrasonic oscillators 28, 30 operate at the same time and in the same rhythm. Due to the combined movements, i.e., the advance of the pipe 22 in the direction of the arrow 26 and the reciprocating motion of the ultrasonic oscillators 28, 30 in the transverse direction, the latter describe essentially sinusoidal test tracks on the pipe 22.

Because of their offset position in space relative to one another, the ultrasonic oscillators 28, 30 cross the weld seam 20 at different times and at different places. This arrangement is selected in such a way that the two ultrasonic oscillators 28, 30 never scan the weld seam 20 at the same time. The output signals of the two ultrasonic oscillators 28, 30 are processed in the circuit 40 for measured value processing in such a way that measured value changes occurring simultaneously are disregarded. They are commonly caused by vibrations during the manipulation of the pipe or else vibrations of the two ultrasonic oscillators 28, 30 together.

On the other hand, measured value deviations detected by only one ultrasonic oscillator but not by the other are contained in the output signal; they describe geometric variations which should be registered. If an ultrasonic oscillator has registered such a change, then the other ultrasonic oscillator should register a corresponding change either already with a certain lag time before or with the same lag time after. The lag time is the time which passes from when the test track of an ultrasonic oscillator 28 intersects a pipe skin line running parallel to the longitudinal axis 24 of the pipe, e.g., an edge of the weld seam until the next ultrasonic oscillator cuts the same line. In the measured value processing circuit 40, the data coming in successively with this time lag can be summarized by the geometric curve of the weld seam, e.g., by an electrical delay of the signal of the front running ultrasonic oscillator or by measures in the software sector. In this way the information on the weld seam is made more reliable.

Measurement results such as are supplied by the measured value processing circuit 40 are represented in FIGS. 5 and 6 for the case of a pipe defectively shaved on the inside. FIG. 5 shows the curve of the sound running times t for the entry echo (on the top in each case) and for the inner wall echo (on the bottom in each case) for the first ultrasonic oscillator 28, and below it that for the following second ultrasonic oscillator 30, in each case plotted against the path s. The output signals in each case also contain disturbances 58 which—since they occur at the same time for both ultrasonic oscillators—do not appear in the output signal which is shown in FIG. 6. FIG. 6 is a representation of the geometric curve of the pipe cross section in a stretched (not round) representation. The measured length of the hydraulic buffer in each case is represented by crosshatched bars; the local thickness of the pipe wall determined after this is shown by the solid bars. These solid bars are the image of the cross section of the pipe wall studied. One clearly recognizes a sharp edge 60 on the inner wall; a shaving defect is present here. A threshold value circuit connected in series determines whether the edge 60 is a jump lying outside or inside the assigned tolerances. Depending on this the pipe studied is selected.

In the example shown in FIG. 3, the two ultrasonic oscillators 28, 30 are not moved, rather by means of a mechanism according to FIG. 1, only the ultrasonic oscillator 28 is moved back and forth, the ultrasonic oscillator 30 emits outside of the weld seam 20 radially into the pipe 22 and is held rigidly at a free distance from the pipe skin. Its test track is therefore a straight line running parallel to the longitudinal pipe axis 24 on the pipe jacket, as shown in FIG. 3. The second ultrasonic oscillator 30 in this design serves only to remove the disturbances from the values of the first ultrasonic oscillator.

The arrangement shown in FIG. 4 with a total of three ultrasonic oscillators 28, 29, 30 designed as separate testing heads and mounted on a common connecting piece 42 as well as the ultrasonic oscillator shown in FIG. 1 are advantageous. As FIG. 4 shows, the three ultrasonic oscillators, as opposed to the example shown in FIG. 1, are also offset axially, arranged in a V pattern. The first ultrasonic oscillator 28 located at the tip of the V is at the front in the direction of motion. The ultrasonic oscillator 30 arranged to the left and above it and behind it in the direction of motion describes a test track, indicated by points, which coincides exactly in the region of crossing of the weld seam 20 in its back movement with the test track of the first ultrasonic oscillator 28. An axial offsetting such as is shown in FIG. 2 does not occur here. In other words, both ultrasonic oscillators 28, 28 cover exactly the same (obliquely running) cross section through the pipe wall. This is true for the backward motion, therefore in the drawing in FIG. 4, the downward motion. The ultrasonic oscillator 29 is not used for the forward motion, i.e., the upward motion, but rather the ultrasonic oscillator 30 arranged to the left below and behind the ultrasonic oscillator 28. It is arranged at a geometrically identical distance to that of the ultrasonic oscillator 29 with the consequence that the lag times are identical in each case. This second ultrasonic oscillator 30 now describes a test track shown as a broken line which coincides partially with that of the first ultrasonic oscillator 28 but with the already discussed time lag.

This arrangement has the advantage, in addition to the already described registration of the same cross-sectional curve, that the measured values of the individual ultrasonic oscillators can be summarized into a common measured value in simplified form, as is the case in the example shown in FIGS. 1 and 2. In the examples shown in FIGS. 1 and 2, it is necessary for a common registration of the forward motions to allow for the altered time relationships and sequence relative to the backward motion. This is not necessary in the example shown in FIG. 4.

In the arrangement in FIG. 7, several ultrasonic oscillators 28 through 30 (of which only 8 are shown) form a test head in the form of an array which is designed here as a phased array. The individual ultrasonic oscillators of the array are arranged on an arc of a circle whose midpoint coincides with the longitudinal axis 24 of the pipe. Their central beams intersect at a point on the longitudinal axis 24 of the pipe. The array is acoustically coupled to the outer wall of the pipe 22 via a hydraulic buffer (not shown). The array extends over an angular range which is larger than that of the angular range occupied by the weld seam. This assures that the array can emit sound on both sides outside of the weld seam in the (undisturbed) region of the pipe 22.

In practical operation, an operating sequence is achieved as has already been described with reference to the first example. The ultrasonic oscillators, however, do not move: the array remains stationary. The pipe 22 is moved in its axial direction (arrow 26). The acoustic entry zone 41 is controlled electronically in such a way that it travels back and forth over the weld seam, the location of all acoustic entry zones 41, 43 is the scanning line on the outer skin, shown as a broken line. Depending on the scanning rate used the scanning is conducted in such a way that either (according to the first example) scanning is performed progressively back and forth or after every n-th scan another acoustic entry zone 43 is moved to, which lies safely outside the weld seam 22, to obtain a reference value.

It should not go without mention that according to the stated process not only weld seams 22 running parallel to the longitudinal axis 24 of the pipe but also weld seams lying on a helical line can be tested.

We claim:

1. A method for ultrasonic measurement of a wall thickness curve of a welded pipe with a weld seam, the method comprising:

coupling a first ultrasonic oscillator to said pipe via a hydraulic buffer, the first ultrasonic oscillator being operable to produce pulses along a radial line toward an outer surface of the pipe;

subjecting said pipe to said ultrasonic pulses in an acoustic entry zone in said pipe;

receiving reflected components of said ultrasonic pulses by said first ultrasonic oscillator and coupling the reflected components as electrical signals to a measured value processing circuit;

moving said first ultrasonic oscillator relative to said pipe, parallel to a pipe axis, and moving the acoustic entry zone on the outer surface of the pipe, back and forth in such a way as to pass repetitively from sensing a peripheral region on one side of the weld seam, over said weld seam to a peripheral region on an opposite side of said weld seam, by said first ultrasonic oscillator;

arranging a second ultrasonic oscillator, coupled acoustically to said pipe via a hydraulic buffer, in a vicinity of said first ultrasonic oscillator, the second ultrasonic oscillator being operable to produce pulses along a radial line toward the outer surface of the pipe;

exposing said pipe to the ultrasonic pulses of the second ultrasonic oscillator such that reflected components of said ultrasonic pulses of the second ultrasonic oscillator are also sent as electrical signals to the measured value processing circuit; and, moving said second ultrasonic oscillator axially relative to said pipe together with said first ultrasonic oscillator, such that only one of said first and second ultrasonic oscillators can ever be above and sensing the weld seam at any given time and that the electrical signals of said first and second ultrasonic oscillators are processed in said measured value processing circuit in such a way that variations present in the electrical signals which occur both in the electrical signal of said first ultrasonic oscillator and also in the electrical signal of said second ultrasonic oscillator, for a given position transverse of the pipe axis, do not appear in the output signal.

2. The method according to claim 1, wherein said first and second ultrasonic oscillators are arranged sufficiently close together that a distance between said acoustic entry zones is not greater than twice a width of said weld seam.

3. The method according to claim 1, wherein said first and second ultrasonic oscillators are rigidly connected relative to one another and are moved together.

4. The method according to claim 1, wherein said first and second ultrasonic oscillators are moved at a distance of 3 to 30 millimeters from an outer surface of the pipe, back and forth without contacting it.

5. The method according to claim 1, wherein said first and second ultrasonic oscillators are offset geometrically and are moved relative to the pipe such that said first and second ultrasonic oscillators successively describe a same test track upon crossing said weld seam.

6. The method according to claim 1, wherein said first and second ultrasonic oscillators are moved back and forth over said weld seam, successive incoming signals of said first and second ultrasonic oscillators being combined into a common signal over a curve of the wall thickness.

7. The method according to claim 1, wherein a plurality of said first and second ultrasonic oscillators are combined to form a test head in the form of an array.

8. An apparatus for implementation of an ultrasonic measuring process, comprising:

a mechanism for guidance and axial conveying of a welded pipe and the apparatus relative to one another;

a first ultrasonic oscillator arranged on a first moving device having means for moving the first ultrasonic oscillator back and forth transversely relative to a weld seam of said welded pipe, said first ultrasonic oscillator forming a hydraulic buffer between itself and said welded pipe, and being connected to a measured value processing circuit operable to produce an output, said first ultrasonic oscillator being operable to produce pulses along a radial line toward an outer surface of the pipe;

at least one second ultrasonic oscillator arranged in close proximity to said first ultrasonic oscillator, said second oscillator forming a hydraulic buffer between itself and said welded pipe and being connected to the measured value processing circuit, said second ultrasonic oscillator being operable to produce pulses along a radial line toward the outer surface of the pipe;

means for passing at least one of the first and second oscillators outside said weld seam back and forth across the longitudinal axis of said welded pipe while crossing said at least one of the first and second oscillators from sensing a peripheral region on one side of said weld seam, over said weld seam, into a peripheral region on an opposite side of said weld seam and only one of said first and second oscillators being over and sensing the weld seam at any given time; and, wherein variations in the electrical signals coupled to said measured value processing circuit for a given position on the welded pipe and which occur both in the electrical signal of said first ultrasonic oscillator and in the electrical signal of said second ultrasonic oscillator do not appear in the output.

9. An apparatus for implementation of an ultrasonic measuring process for a welded pipe having a weld seam, comprising:

a mechanism for guidance and axial conveying of the welded pipe and the apparatus relative to one another;

a first ultrasonic oscillator providing an acoustic entry zone on said welded pipe that is moved back and forth across said weld seam of said welded pipe from sensing a peripheral region on one side of the weld seam, over the weld seam, to a peripheral region on an opposite side of the weld seam, said first ultrasonic oscillator forming a hydraulic buffer between itself and said welded pipe and being connected to a measured value processing circuit providing an output, said first ultrasonic oscillator being operable to produce pulses along a radial line toward an outer surface of the pipe;

a number of additional ultrasonic oscillators connected to form an array with said first ultrasonic oscillator and also forming a hydraulic buffer between said additional ultrasonic oscillators and said welded pipe, outputs of the additional ultrasonic oscillators providing electrical signals coupled to said measured value processing circuit, said array formed from said ultrasonic oscillators being held stationary and covering an angular range larger than an angular range of said weld seam, said additional ultrasonic oscillator being operable to produce pulses along a radial line toward an outer surface of the pipe; and, wherein in said measured value processing circuit, variations first ultrasonic oscillator and in the electrical signal of said additional ultrasonic oscillators for a given position on the welded pipe do not appear in the output of the measured value processing circuit.

10. The apparatus of claim 9, wherein said array formed from said additional ultrasonic oscillators is curved as an arc of a circle having a midpoint of curvature that lies on a longitudinal axis of said welded pipe, and center beams of said additional ultrasonic oscillators intersect at a point on said longitudinal axis of said welded pipe.

11. The method of claim 1, wherein said welded pipe comprises a shaved weld seam.

12. The method of claim 4, wherein said first and second ultrasonic oscillators are moved at a distance of 5 to 12 millimeters from the outer edge of the pipe.

13. The method of claim 7, wherein said array is a phased array, and further comprising modulating the phased array for moving the acoustic entry zone thereof, transversely of the pipe axis.

14. The apparatus of claim 8, further comprising a second moving device upon which the second ultrasonic oscillator is arranged, the second moving device having means for moving the second ultrasonic oscillator back and forth transversely relative to a weld seam of said welded pipe, wherein said second moving device is identical in size with said first moving device.

15. The apparatus of claim 9, wherein said array formed by said additional ultrasonic oscillators is a phased array and further comprising means for modulating the phased array such that the acoustic entry zone of the array is moved transversely of a pipe axis.

* * * * *